United States Patent [19]

Lamb et al.

[11] Patent Number: 4,911,177

[45] Date of Patent: Mar. 27, 1990

[54] DYNAMIC SAGITTAL KNEE TEST APPARATUS

[76] Inventors: Steve Lamb, 6724 Corte Del Vista, Pleasanton, Calif. 94566; Larry W. Lamoreux, 5470 Manila Ave., Oakland, Calif. 94618

[21] Appl. No.: 281,179

[22] Filed: Dec. 7, 1988

[51] Int. Cl.<sup>4</sup> ............................................. A61B 5/10
[52] U.S. Cl. ....................................... 128/782; 33/512
[58] Field of Search .................. 128/774, 782; 73/379; 33/511, 512

[56] References Cited

U.S. PATENT DOCUMENTS

| | | | |
|---|---|---|---|
| 4,306,571 | 12/1981 | McLeod, Jr. | 128/782 |
| 4,436,099 | 3/1984 | Raftopoulos | 128/782 |
| 4,534,364 | 8/1985 | Lamoreux | 128/774 |
| 4,804,000 | 2/1989 | Lamb et al. | 128/774 |

FOREIGN PATENT DOCUMENTS 1175434A 8/1985 U.S.S.R. ............................... 128/774

*Primary Examiner*—Max Hindenburg
*Assistant Examiner*—Randy Shay
*Attorney, Agent, or Firm*—Bielen, Peterson & Lampe

[57] ABSTRACT

An improved dynamic sagittal knee test apparatus having a skeletal frame structure with a thigh portion attachable to a patient's thigh, a shin portion attachable to a patient's shin and an interconnecting spanning linkage portion connecting the thigh portion to the shin portion, the interconnecting linkage assembly having three axial transducers for measuring arcuate displacements on three primary perpendicular axes for measuring leg flexion, varus-valgus angular displacement, and axial rotation of the tibia relative to the femur, the three transducers being arranged to take measurements without reconfiguration of linkage in the spanning link portion of the test apparatus, the apparatus including a patella assembly with an additional transducer for measuring anterior-posterior displacements of the tibia relative to the femur.

9 Claims, 2 Drawing Sheets

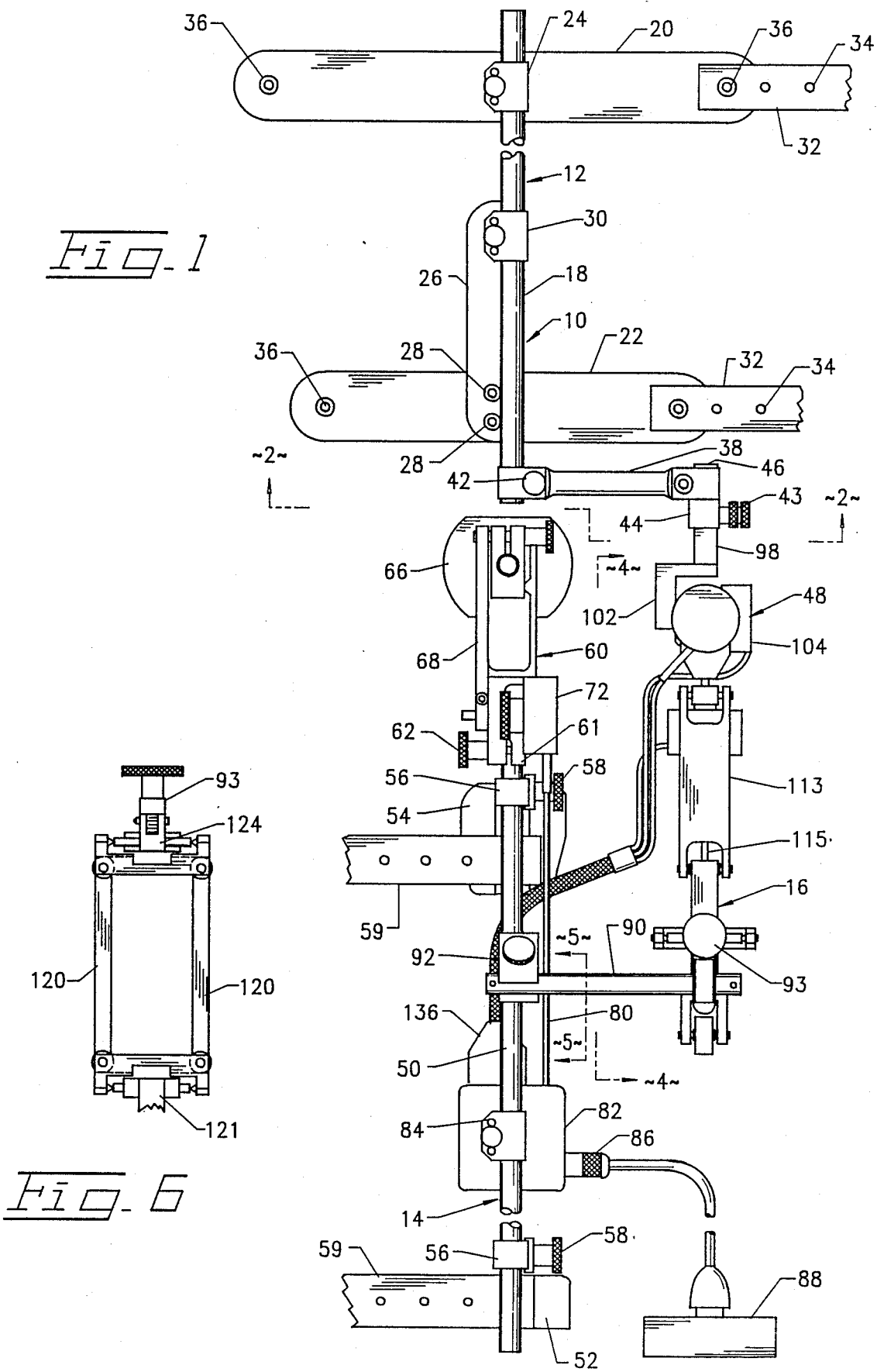

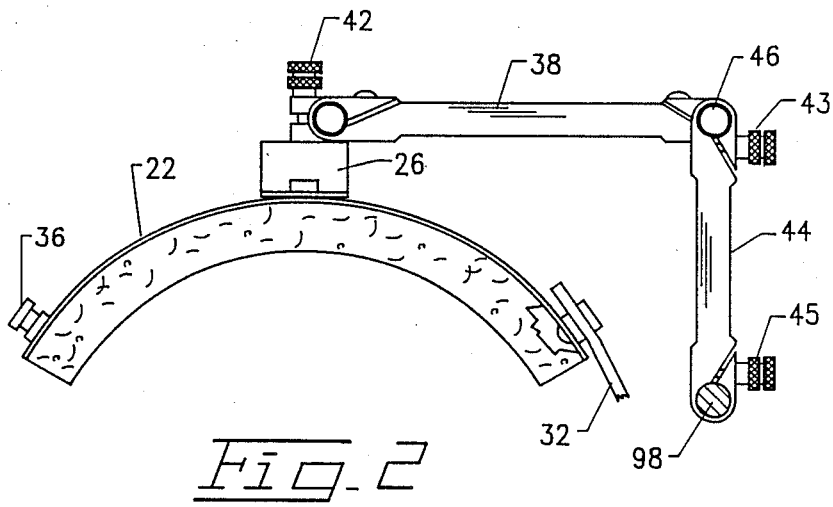
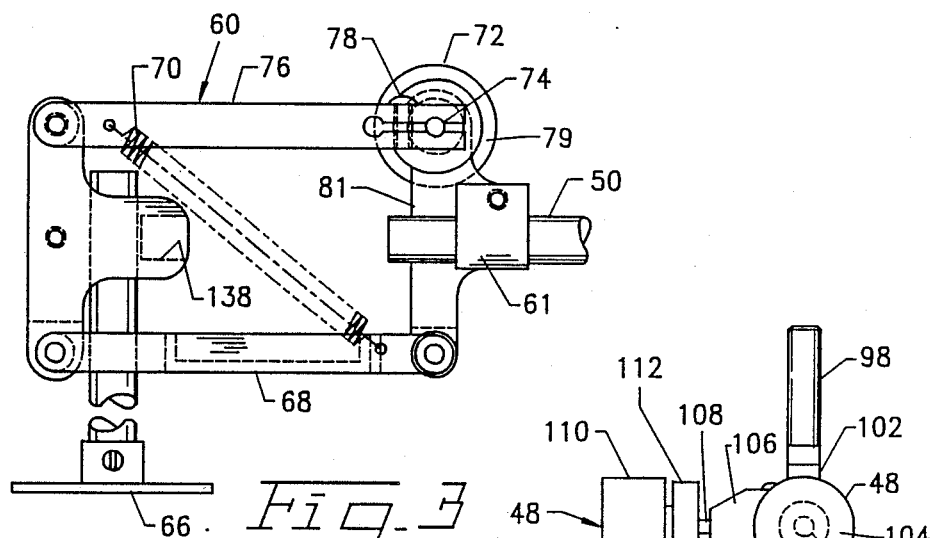
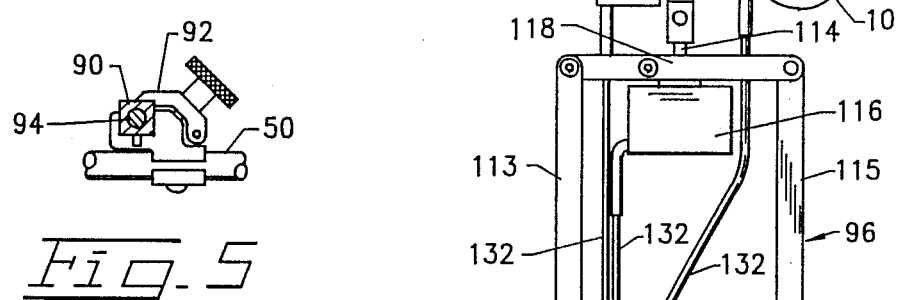
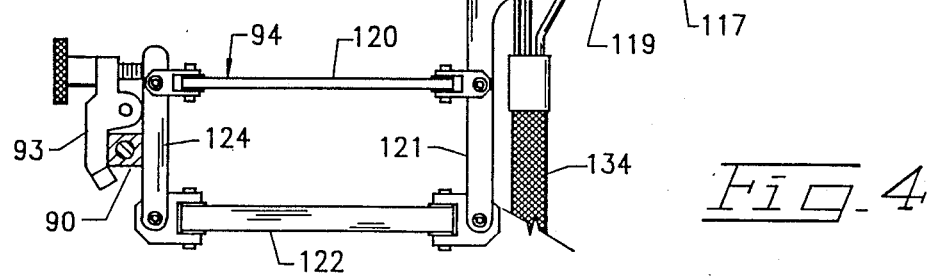

DYNAMIC SAGITTAL KNEE TEST APPARATUS

BACKGROUND OF THE INVENTION

This invention relates to improvement in dynamic sagittal knee test apparatus. Our prior apparatus described in U.S. patent application Ser. No. 005,921, filed Jan. 21, 1987, entitled, DYNAMIC SAGITTAL KNEE TEST APPARATUS disclosed a sagittal knee test apparatus that can measure knee laxities of a patient in both conventional test situations, wherein the patient is seated on a table and forces are applied to the knee at various leg extensions, or, can be utilized to measure knee and leg conditions while the patient walks in a normal manner. The advantage of such a device is described fully in our prior art application.

In summary, the apparatus for measuring ligamentous insufficiency in the knee enables a physician to provide a diagnosis of injury and/or an evaluation of different treatment methods. In the past, abnormal motion between the tibia and the femur was detected by a physician by manipulation of the leg by hand. Often the motion of a leg with a ligament tear is subtle and difficult to quantify or even compare with the patient's uninjured leg. Because a normal knee may have a substantial motion, it is desirable to quantitatively measure the precise displacement to allow an accurate comparison between the patient's normal and injured knee to determine the likely extent of injury. Further, it is desirable to quantify such measurements to compare motion of the patient's knee with statistical norms or with past records to monitor the progress of treatment.

Both our prior apparatus and the present apparatus are designed to be autoclavable or sterilizable by other methods. The apparatus is designed for use in both the 20° Lachman test and 90° anterior drawer test, and, without refitting is designed for use in measuring posterior excursions. It is believed that measurement of both anterior and posterior excursions provides the physician with the maximum useful data for proper diagnosis and treatment.

Our original mechanical device described in our patent No. 4,534,364 issued Aug. 13, 1985, entitled SAGITTAL KNEE TEST APPARATUS, provides an exoskeletal frame structure that permits comparative measurements to be taken from the light weight frame structure itself, thus freeing the patient from the chair as a reference point and improving the accuracy of measurements. It has been found, however, that measurements in addition to the anterior and posterior displacement are useful in accurately diagnosing the nature and extent of an injury. It is advantageous to measure varus-valgus laxity and axial rotation of the tibia relative to the femur. These additional measurements greatly enhance the ability to correctly determine the severity of injury and in particular whether it is the anterior cruciate ligament, medial collateral ligament or both that are damaged. Our apparatus as descried in the referenced patent application, Ser. No. 005,921, is designed to connect to the patient's leg at the long skeletal prominences with minimum restriction of normal joint motions. The framework is light in weight and mechanically self contained without mechanical connection to an external structure. The apparatus permits ambulatory motion to allow measurement to be obtained during normal movement such as walking as well as during conventional contrived, examination procedures where the leg is manipulated by hand or by special force measuring apparatus as disclosed in said application.

The present improvements relate to the dynamic sagittal knee test apparatus described in application Ser. No. 005,921, and enable the apparatus to be utilized with greater efficiency and ease. Since a prime source of diagnostic information is gained from comparative measurements of the patient's injured knee with the patient's uninjured knee, the sagittal knee test apparatus is frequently removed from one leg and installed on the patient's other leg. It is desirable to have this replacement accomplished as quickly and simply as possible. Furthermore, the complex linkage of the mechanism should be disturbed as little as possible such that accurate conparative tests can be accomplished. In our prior device, the linkage interconnecting the femoral frame and the tibial frame must be reconfigured when changing from varus-valgus tests to axial rotation tests. By integrating certain parts of the linkage, both axial rotation measurements and the varus-valgus rotations can be made at the same time, without having to reconnect the spanning linkage between the femoral mount and the tibial mount. In addition to simplifying the procedures that must be accomplished by the physician, the system allows for measuring to be accomplished in immediate sequence without readjustment of the equipment and potential change in the condition of the patient.

The improved spanning linkage has been devised to accomplish the three desired measurements without readjustment and has been constructed to make the measurements without being being affected by the polycentric motion of the knee during flexure. In this respect the improved linkage assembly incorporates the advantages of the prior assembly while eliminating its primary disadvantage.

SUMMARY OF THE INVENTION

The improved dynamic sagittal knee test apparatus of this invention combines four measuring transducers on a skeletal frame that is attached to a patient's leg from which knee laxity can be determined independent of any external reference structure.

The light weight frame structure is constructed with a femoral portion and a tibial portion that are interconnected by a spanning linkage assembly. The femoral frame includes an elongated rod that is mounted at the front or side of the user's thigh substantially parallel with the femur. Similarly, the tibial portion includes an elongated rod that is mounted over the patient's shin substantially parallel with the tibia. The interconnecting spanning linkage assembly is positioned on the outside of the patient's leg with three rotary measuring transducers located proximate the general axis of the knee during leg flexion.

Because the knee does not operate like a hinge with a single axis of rotation, but rather the tibia moves in a complex motion with respect to the femur, the tibial frame cannot be directly connected to the femoral frame with a single pivot connection. The polycentric motion of the knee results in a piston type action of the tibia with the femur such that any tibial frame structure with a single pivot axis connecting it to a femoral structure would jam as the patient's leg is extended from a bent condition to a straight leg position. The piston action is not a single dimension action because of the swinging motion of the leg. Thus, a single parallelogram, four-bar linkage assembly is inadequate to accommodate for the piston action during the full arc of the tibial motion. However, when two four-bar parallelogram linkage assemblies are interconnected in the same plane with a common 90°, L-shaped link, the piston action can be absorbed in the linkage assembly throughout the arcuate movement of the leg.

The degree of arcuate movement can be detected by a transducer that senses angular displacement. By mounting the transducer to a side extension on the femoral frame with the transducer shaft axis substantially aligned with the moving axis of the knee, and connecting the shaft to the double parallelogram linkage assembly, the angular displacement of the knee during flexion can be determined. Since both of the parallelogram linkages are in the same plane and such plane substantially coincides with the plane of arcuate leg flexion, the spanning assembly is essentially a rigid structure to side displacements of the leg. Thus, mediolateral displacements of the leg can be detected by a second angular displacement measuring transducer that is mounted perpendicular and proximate the first transducer. The two transducers provide a two axis pivotal connection for the tibial frame to the femoral frame via the parallelogram linkage. Finally, to detect axial rotation of the tibia relative to the femur, a third transducer is positioned proximate to the first two transducers with its shaft axis substantially parallel to the tibial rod and perpendicular to the other two measurement axes. Axial rotation of the tibia and tibial frame is transmitted to the spanning linkage assembly by a third parallelogram linkage incorporated into one of the previously described linkages such that the arcuate moment arm displacement of the tibial frame can be translated as an angular twist of the spanning linkage and detected by an appropriately positioned transducer.

The transducers are all connected to a microprocessor which can include any corrective procedures necessary to adjust the sensed angular displacements to the actual relative displacements of the anatomical bone structures.

By incorporating the axial rotation linkage into the flexion linkage, measurements can be taken from the axial rotation transducer, the flexion angle transducer and the varus-valgus angle transducer simultaneously without reconfiguring the spanning linkage structure. This reconfiguration was a substantial disadvantage to our prior structure and prevented simultaneous measurements from being taken, for example during ambulatory movement of the patient.

The knee test frame structure also includes a patella assembly for measuring anterior and posterior displacements of the tibia relative to the femur, particularly when predesignated forces are applied to the tibia. The patella contact assembly utilizes a similar parallel four-bar linkage assembly with in this instance the fourth transducer for measuring angular displacements being utilized as one of the pivots in the linkage assembly such that linear displacements of the patella are translated into angular displacements. Again, the microprocessor includes the necessary programming to retranslate sensed angular displacements into appropriate linear measurements.

The improved structured disclosed both abbreviates the time required for accomplishing traditional diagnostic procedures and provides a device enabling development of entirely new diagnostic procedures.

BRIEF DESCRIPTION OF THE DRAWINGS

FIG. 1 is a front elevational view of the knee test apparatus as it would be positioned on a fully extended leg of a patient.

FIG. 2 is a partial cross sectional view taken along the lines 2—2 in FIG. 1.

FIG. 3 is a partial side elevational view of the patella measuring assembly.

FIG. 4 is a side elevational view partially in cross section of the spanning link assembly taken on the lines 4—4 in FIG. 1.

FIG. 5 is a partial cross sectional view taken along the lines 5—5 in FIG. 1.

FIG. 6 is a top view partially fragmented of a portion of the spanning link assembly of FIG. 1.

DETAILED DESCRIPTION OF THE PREFERRED EMBODIMENTS

Referring to FIG. 1, the improved dynamic knee test apparatus designated by the reference numeral 10 is shown in an extended position. The apparatus is essentially a skeletal structure that includes an upper thigh portion 12 and a lower leg portion 14 with an interconnecting spanning link portion 16. The thigh portion 12 and the lower leg portion 14 are essentially identical to the dynamic knee test apparatus described in U.S. patent application No. 005,921, filed Jan. 21, 1987. The interconnecting spanning link portion 16 includes an improved linkage and transducer assembly to enable both tibial rotation and varus-valgus moment angulation to be determined without reconfiguring the linkage assembly.

The thigh portion or femoral frame 12 includes a femoral rod 18 with an arcuate upper pad member 20 and a lower pad member 22. The upper pad member 20 is directly connected to a clamp 24 that secures the upper pad to the femoral rod 18. The lower pad 22 is connected to a flat displacement leaf 26 by fasteners 28 at one end and at a clamp member 30 at the other end such that the lower pad 22 seats on the thigh above the knee and positions the femoral rod above the leg substantially parallel with the axis of the femur. When the pads are properly spaced and positioned on the patient's thigh the thigh portion of the knee test apparatus is secured in place by straps 32 which encircle the thigh and include holes 34 that engage short posts 36 to hold the femoral rod securely in position on the thigh.

At the end of the femoral rod 18 is a side bar member 38 which displaces the interconnecting spanning link assembly 16 to the side of the patient's leg. The side bar member 38 is connected to the end of the femoral rod 18 by a thumb screw clamp 42. A substantially perpendicular member 44 connected to the end of the side bar member 38 by a short rod 46 such that its distal end locates a transducer assembly 48 proximate the general extension axis of the patient's knee. The perpendicular member 44 has thumb screw clamps 43 and 45 to facilitate adjustments. While precise location is not required, close positioning to the shifting axis of the knee insures minimal accommodating movements of the parallelogram linkage elements.

Similarly, the lower leg portion or tibial frame 14 is essentially identical to that previously described in the reference application. The lower tibial frame 14 includes a tibial rod 50 with a lower pad 52 that seats on the bony portion of the shin just above the ankle and an upper pad 54 that seats on the tibial tubercle, a stable location proximate the patella. The pads can be positioned by slidable posts 56 with thumb screws 58 and the tibial frame secured by straps 59. The tibial rod 50 provides a mounting post for the patella pad assembly 60 which is connected to the end of the tibial rod by insertion into a shaft seat 61 and tightening of a thumb screw 62. The patella contact assembly 60 includes a patella pad 66 carried on a parallelogram linkage assembly 68 and urged toward the patient's patella by bias spring 70. The displacement of the patella pad is detected by a transducer 72 that detects the angular position of its sensing shaft 74 that is clamped to one of the parallel links 76 by a clamping screw 78 while its housing 79 is mounted to the connected link 81 as shown in FIG. 3. All transducers in the test apparatus are essentially identical and detect axial displacements of their shafts relative to their housings. Fore and aft displacements of the patella pad during diagnostic procedures are detected as angular displacements and translated in an associated microprocessor as described in the referenced application.

The transducer 72 is connected by electrical line 80 to a plug terminal 82 mounted on the tibial rod 50 by clamp 84. The plug terminal 82 has a socket for a multi-line connector 86 which electrically connects the knee test assembly 10 to an auxiliary microprocessor 88 shown schematically in FIG. 1.

The improved spanning link portion 16 of the frame structure interconnects the thigh portion and the lower leg portion. The interconnecting spanning link assembly is connected, at one end to the vertical perpendicular 44 by thumb screw clamp 45 and at the other end to a cross member 90 on the tibial frame 14 by a quick release thumb screw clamp 93. The cross member 90 is secured to the tibial rod 50 by locking clamp 92 that has a prong engagement member 94 to secure the cross member in position as shown in FIG. 5.

Referring to FIGS. 1 and 4, the spanning length portion 16 of the frame structure includes a first, three-dimensional linkage 94 connected to a two dimensional linkage 96 such that the various angular displacements to be sensed are not affected by the non-axial motion of the knee when the patient's leg moves from a bent to a straight position or vice-versa. The spanning link assembly 16 has a mounting post 98 which connects to the vertical member 44 of the femoral frame 12 and is secured thereto by clamp 45. The post 98 is connected to a bracket 102 that is engaged with the shaft 100 (shown in dotted line) of flexion angle transducer 104. The flexion angle transducer 104 measures the degree of flex or extension of the knee. The flexion angle transducer 104 is mounted to a carrier 106 that engages the shaft 108 of the varus-valgus transducer 110 for determining varus-valgus displacement. This medio-lateral displacement is angular in form and is determined by holding the knee of a seated patient steady while the leg is straight, usually at 0° to 5° angle, applying a side-ways displacing force on the lower portion of the tibia.

The varus-valgus transducer 110 is mounted to a carrier 112 having a connection to the shaft 114 of the rotation transducer 116, which is mounted to the top link 118 of the four-bar link assembly 96. The two-dimensional linkage assembly 96 includes the mounting link 118, two parallel side links 113, 115 and an L-shaped connecting link 117 having an arm segment 119 parallel to the mounting link 118 such that a parallelogram linkage is formed. The other arm 121 of the L-shaped connecting link 117 forms one of the links for the three-dimensional linkage assembly 94.

The three-dimensional linkage assembly 94 allows the axial rotation of the tibia that is imparted to the tibial frame to be translated to the two-dimensional linkage 96 by action of the two pivotally connected parallelogram links 120 shown also in the partial view of FIG. 6 to the two dimensional linkage assembly 96. This rotational motion is imparted to the rotation transducer 116 and sensed because of the relatively fixed position of the transducer shaft 114 that is connected to the stationary thigh frame 12. The compound pivotally connected link 122 opposite the two opposed links 120 is connected to end links 124 and 121 to allow the irregular translational motions of the tibia during knee flexion to be absorbed by the double linkage assemblied 94 and 96 without affecting the axial rotation being sensed. The three-dimensional linkage 94 essentially has two parallel linkage assemblies in perpendicular planes whereas the two-dimensional linkage 96 is restricted to a single plane. Both assemblies share the common L-shaped double link member 117.

The flex potentiometer 104 is positioned proximate the general axis of knee flexion which as noted moves as the leg is extended. This alignment minimizes the motions of the parallelogram required to accommodate the fact that the knee flexion is not truly axial but is polycentric in nature. Electrical leads 132 from each of the transducers are joined in a common harness 134 and connected to the terminal 82 by a plug 136.

When the knee test assembly 10 is removed and shifted to the other leg of the user, the spanning line assembly 16 can be disconnected at the lower end detaching the quick disconnect clamps 92 and 93 and sliding cross member 90 to the opposite side, and by loosening femoral rod clamps 42 and 43 to swing the spanning link assembly to the other side of the thigh and lower leg portions of the assembly. The spanning link portion is thereby repositioned on the outside of the user's other leg for taking similar measurements and reconnected at its lower end. As noted, the improved knee test assembly of this invention can be used with the auxiliary components described in the referenced application or be used in advanced test procedures where the patient walks during simultaneous sampling by the three transducers on the spanning link assembly. In such ambulatory tests, the patella pad can be engaged, or alternately locked in its retracted position by extending the tibial rod 50 into a socket 138 in the patella pad assembly. This is the position for zero setting of the patella transducer 72.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. In a dynamic sagittal knee test apparatus for measuring knee laxities of a patient the test apparatus having:

a femoral frame with an elongated rod element having mounting means for securely mounting the femoral rod element to the anterior portion of a patient's thigh with the rod element fixed in position relative to the thigh along the femur; and a tibial frame with an elongated rod element having mounting means for securely mounting the tibial rod element to the anterior portion of a patient's shin with the rod element fixed in position relative to the shin along the tibia; and the improvement comprising: a spanning linkage assembly having a first end connected to the femoral frame and a second end connected to the tibial frame with means for accommodating displacement differentials occasioned by non-axial motion of the patient's knee on flexion, the spanning linkage assembly including a first transducer means for measuring the angle of flexion of the tibia relative to the femur, a second transducer means for measuring the angle of varus-valgus movement of the tibia relative to the femur, and a third transducer means for measuring the angle of axial rotation of the tibia relative to the femur, wherein the configuration of the three transducer means with the linkage assembly includes means for enabling measurements to be taken from each transducer means simultaneously or separately without reconfiguring the linkage assembly.

2. The improvement of claim 1 wherein the spanning linkage assembly includes a three-dimensional parallelogram linkage assembly connected to a two dimensional parallelogram linkage assembly.

3. The improvement of claim 2 wherein the three-dimensional linkage assembly has a compound first, four-bar parallel linkage and second, four-bar parallel linkage having a plane perpendicular to the plane of the first linkage, and the two-dimensional linkage assembly has a four-bar parallel linkage in the same plane with the second parallel linkage of the three-dimensional linkage assembly and has a common L-shaped link member with the second parallel linkage of the three-dimensional linkage assembly.

4. The improvement of claim 1 wherein the first, second and third transducer means are located in a transducer assembly adapted to be proximate the knee with each transducer means having an angular displacement sensing shaft substantially perpendicular to the other shafts for measuring angular displacements on three primary axes, the transducer assembly being fixed from relative linear movement to the femoral frame.

5. The improved apparatus of claim 4 wherein the means for accommodating displacement differentials occasioned by non-axial motion of the patient's knee on flexion comprises a double four-bar, parallelogram linkage assembly having a common interconnecting L-shaped link wherein the double linkage assembly is formed with two four-bar, parallel linkages interconnected in the same plane, perpendicular to one another by the L-shaped link.

6. The improvement of claim 5 wherein the tibial frame has a side member and wherein one of the two four-bar linkages is connected to the transducer assembly and the other of the two four-bar linkage is connected to the side member of the tibial frame with the two four-bar linkages arranged during use in a plane substantially parallel to the plane of a patient's leg flexion.

7. The improvement of claim 6 comprising further a third four-bar, parallel linkage interconnected with the four-bar linkage that is connected to the side member of the tibial frame and arranged in a plane perpendicular thereto, wherein axial rotation of the patient's tibia is transmitted from the tibial frame through the third four bar linkage to the third transducer means when the test apparatus is in use.

8. The improvement of claim 7 wherein each of the transducers comprises an axial transducer with a housing and a projecting shaft rotatable relative to the housing wherein angular displacements are detected by the transducers by rotation of the transducer shaft relative to the transducer housing.

9. The improved apparatus of claim 1 wherein the tibial frame includes a patella contact assembly with fourth transducer means for measuring anterior and posterior displacements of the tibia relative to the femur.

* * * * *